(12) United States Patent
Sekeljic et al.

(10) Patent No.: US 10,830,615 B2
(45) Date of Patent: Nov. 10, 2020

(54) BEND ANGLE SENSING SYSTEMS AND RELATED METHODS

(71) Applicant: Intel Corporation, Santa Clara, CA (US)

(72) Inventors: Nada Sekeljic, Hillsboro, OR (US); Suraj Sindia, Hillsboro, OR (US); Zhen Yao, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 473 days.

(21) Appl. No.: 15/721,669

(22) Filed: Sep. 29, 2017

(65) Prior Publication Data

US 2019/0101415 A1   Apr. 4, 2019

(51) Int. Cl.

| G01B 7/14 | (2006.01) |
|---|---|
| G01B 7/30 | (2006.01) |
| H01F 5/00 | (2006.01) |
| G01D 5/20 | (2006.01) |
| A61B 5/11 | (2006.01) |
| A61B 5/00 | (2006.01) |
| A61B 5/05 | (2006.01) |
| A61B 5/107 | (2006.01) |
| G01B 7/00 | (2006.01) |
| G01B 11/14 | (2006.01) |

(52) U.S. Cl.
CPC ......... *G01D 5/2066* (2013.01); *A61B 5/0015* (2013.01); *A61B 5/0024* (2013.01); *A61B 5/05* (2013.01); *A61B 5/1071* (2013.01); *A61B 5/1121* (2013.01); *A61B 5/6803* (2013.01); *A61B 5/6824* (2013.01); *A61B 5/7278* (2013.01); *G01D 5/20* (2013.01); *G01D 5/2013* (2013.01); *G01D 5/2046* (2013.01); *G01D 5/2073* (2013.01); *A61B 5/6831* (2013.01); *G01B 7/003* (2013.01); *G01B 7/14* (2013.01); *G01B 7/30* (2013.01); *G01B 11/14* (2013.01)

(58) Field of Classification Search
CPC ...... G01D 5/2046; G01D 5/20; G01D 5/2073; G01D 5/2013; G01B 7/003; G01B 7/14; G01B 7/30; G01B 11/14
USPC ..... 324/51, 55, 200, 207.11, 207.13, 207.15, 324/207.16, 207.17
See application file for complete search history.

(56) References Cited

U.S. PATENT DOCUMENTS

2007/0257667 A1* 11/2007 Schroeder ............ G01D 5/2073
                                                                 324/207.17
2016/0238731 A1*  8/2016 Chopra ................. H02J 7/0042
(Continued)

OTHER PUBLICATIONS

Fujita et al.; "Electromagnetic Characteristics of Body Area Network Using Magnetically-Coupled Wearable Coils Worn on Bent Arm." Proc. of 2016 International Conference on Electronics Packaging (ICEP); Apr. 2016; pp. 656-659.
(Continued)

*Primary Examiner* — Raul J Rios Russo
(74) *Attorney, Agent, or Firm* — Schiff Hardin LLP

(57) ABSTRACT

Systems and methods for sensing angular displacement between body segments of users include disposing an electromagnetic transmitting sensor about a first body segment and an electromagnetic receiving sensor about a second body segment. Data related to the magnetic field coupling between the transmitting and receiving sensors can be captured for determining the angular displacement between the first and second body segments.

26 Claims, 15 Drawing Sheets

(56) References Cited

U.S. PATENT DOCUMENTS

| | | | | |
|---|---|---|---|---|
| 2016/0294112 | A1* | 10/2016 | Edidin | A61B 1/00105 |
| 2016/0370441 | A1* | 12/2016 | Goodson | G01R 33/0023 |
| 2017/0059361 | A1* | 3/2017 | Nagarkar | G01D 5/16 |
| 2018/0214215 | A1* | 8/2018 | Leo | A61B 5/065 |
| 2019/0025089 | A1* | 1/2019 | Elliott | G01D 5/2225 |

OTHER PUBLICATIONS

Gabriel et al.; "The Dielectric Properties of Biological Tissues: II. Measurements in the Frequency Range 10 Hz to 20 GHz." Physics in Medicine & Biology; IOP Science; Nov. 1996; vol. 41, Issue 11; pp. 2251-2269.

Hong et al.; "Noncontact Proximity Vital Sign Sensor Based on PLL for Sensitivity Enhancement." IEEE Trans. On Biomedical Circuits and Systems; IEEE; Nov. 4, 2013; vol. 8, Issue 4; pp. 584-593.

Lee et al.; "Dual-Mode Capacitive Proximity Sensor for Robot Application: Implementation of Tactile and Proximity Sensing Capability on a Single Polymer Platform Using Shared Electrodes." IEEE Sensors Journal; IEEE; Oct. 23, 2009; vol. 9, Issue 12; pp. 1748-1755.

Park et al.; "Magnetic Human Body Communication." Proc. of the IEEE 2015 $37^{th}$ Annual International Conference; Aug. 2015; pp. 1841-1844.

Quam.; "Gesture Recognition with a DataGlove." Proc. of the IEEE 1990 National Aerospace and Electronics Conference (NAECON); May 1990; pp. 755-760.

Vicon; "Intelligence in Motion." Est. 1984 Oxford, UK; https://www.vicon.com/; 2 Pages.

Vicon Industries; "Roughneck™ and Surveyor2000™ Fixed Camera Domes with Non-Isolated Power Inputs." Technical Bulletin; 2000; 4 Pages.

Wikipedia.; "Wired Glove." http://en.wikipedia.org/wiki/Wired_glove; 4 Pages.

You et al.; "Hybrid Inertial and Vision Tracking for Augmented Reality Registration." Proc. of the IEEE 1999 Virtual Reality Conference; Mar. 1999; 8 Pages.

* cited by examiner

BEND ANGLE SENSING SYSTEMS AND RELATED METHODS

BACKGROUND

Many activities that involve body movement, performance, or positioning can benefit from measuring angles between body segments. Non-limiting examples include sports biomechanics, office ergonomics for repetitive stress injury avoidance, physical therapy, medical diagnostics, accident prevention and mitigation, as well as prosthetics design and fitting. Some conventional techniques for measuring body movement include camera based systems, glove bases systems, inertial sensor based systems, and capacitive coupling sensors. Each technology has various advantages and disadvantages. For example, camera based Human Activity Recognition (HAR) systems can capture whole-body motion with a high degree of accuracy. However, the technique is computationally intensive and such systems are not typically mobile and have a limited field of view.

Accordingly, additional HAR techniques that can measure bending angles with a relatively high degree of accuracy, relatively low complexity, and which can be used alone or in combination with other HAR techniques are desirable.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein.

DESCRIPTION OF EMBODIMENTS

Figure 1:
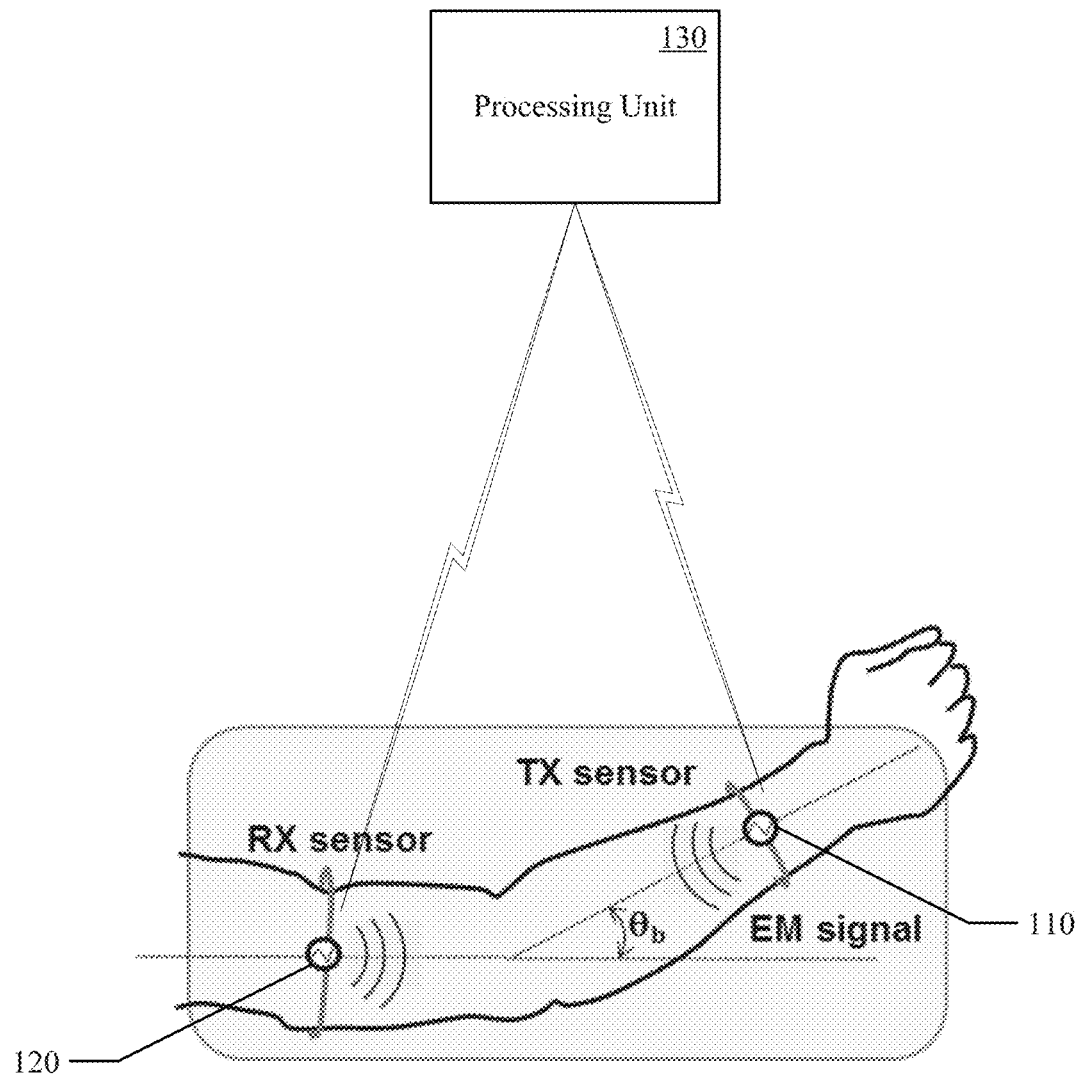
FIG. 1 is a diagram of a system for sensing bending angles through magnetic field coupling in accordance with an example embodiment.

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to convey a thorough understanding of various invention embodiments. One skilled in the relevant art will recognize, however, that such detailed embodiments do not limit the overall inventive concepts articulated herein, but are merely representative thereof.

As used in this written description, the singular forms "a," "an" and "the" include express support for plural referents unless the context clearly dictates otherwise. Thus, for example, reference to "a sensor" includes a plurality of such sensors.

Reference throughout this specification to "an example" means that a particular feature, structure, or characteristic described in connection with the example is included in at least one invention embodiment. Thus, appearances of the phrases "in an example" or "in an embodiment" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various invention embodiments and examples can be referred to herein along with alternatives for the various components thereof. It is understood that such embodiments, examples, and alternatives are not to be construed as de facto equivalents of one another, but are to be considered as separate and autonomous representations under the present disclosure.

Furthermore, the described features, structures, or characteristics can be combined in any suitable manner in one or more embodiments. In the following description, numerous specific details are provided, such as examples of layouts, distances, network examples, etc., to provide a thorough understanding of invention embodiments. One skilled in the relevant art will recognize, however, that the technology can be practiced without one or more of the specific details, or with other methods, components, layouts, etc. In other instances, well-known structures, materials, or operations may not be shown or described in detail to avoid obscuring aspects of the disclosure.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a data region that has an "increased" risk of corruption can refer to a region of a memory device, which is more likely to have write errors to it than other regions in the same memory device. A number of factors can cause such increased risk, including location, fabrication process, number of program pulses applied to the region, etc.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases, depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

Numerical amounts and data may be expressed or presented herein in a range format. It is to be understood, that such a range format is used merely for convenience and brevity, and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

As used herein, the term "circuitry" can refer to, be part of, or include an Application Specific Integrated Circuit (ASIC), an electronic circuit, a processor (shared, dedicated, or group), and/or memory (shared, dedicated, or group) that execute one or more software or firmware programs, a combinational logic circuit, and/or other suitable hardware components that provide the described functionality. In some aspects, the circuitry can be implemented in, or functions associated with the circuitry can be implemented by, one or more software or firmware modules. In some aspects, circuitry can include logic, at least partially operable in hardware.

Various techniques, or certain aspects or portions thereof, may take the form of program code (i.e., instructions) embodied in tangible media, such as floppy diskettes, compact disc-read-only memory (CD-ROMs), hard drives, transitory or non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a random-access memory (RAM), erasable programmable read only memory (EPROM), flash drive, optical drive, magnetic hard drive, solid state drive, or other medium for storing electronic data. The node and wireless device may also include a transceiver module (i.e., transceiver), a counter module (i.e., counter), a processing module (i.e., processor), and/or a clock module (i.e., clock) or timer module (i.e., timer). One or more programs that may implement or utilize the various techniques described herein may use an application programming interface (API), reusable controls, and the like. Such programs may be implemented in a high-level procedural or object oriented programming language to communicate with a computer system. However, the program(s) may be implemented in assembly or machine language, if desired. In any case, the language may be a compiled or interpreted language, and combined with hardware implementations.

As used herein, the term "processor" can include general purpose processors, specialized processors such as central processing units (CPUs), graphics processing units (GPUs), digital signal processors (DSPs), microcontrollers (MCUs), embedded controller (ECs), field programmable gate arrays (FPGAs), or other types of specialized processors, as well as base band processors used in transceivers to send, receive, and process wireless communications.

It should be understood that many of the functional units described in this specification may have been labeled as modules, in order to more particularly emphasize their implementation independence. For example, a module may be implemented as a hardware circuit comprising custom very-large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module may not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

EXAMPLE EMBODIMENTS

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

Systems for sensing bending angles between body segments can include a transmitting sensor and a receiving sensor. The body segments may include for example, the arm and forearm of a user, the thigh and ankle of a user, or other body segments joined by one or more joints such as the elbow, shoulder, wrist, neck, waste, knee, ankle, or knuckles. The transmitting sensor can include a first set of one or more coils adapted to be disposed about a first body segment. The transmitting sensor can also include a current source to drive a current through the first set of one or more coils to radiate an electromagnetic field. The receiving sensor can include a second set of one or more coils adapted to be disposed about a second body segment. The receiving sensor can also include a voltage sensor to determine an open circuit voltage induced in the second set of one or more coils by the electromagnetic field radiated from the first set of one or more coils. Alternatively, the receiving sensor can also include a current sensor to determine a current induced in the second set of one or more coils by the electromagnetic field radiated from the first set of one or more coils. A processing unit can measure an angular displacement between the first and second body segments as a function of the open circuit voltage induced in the second set of one or more coils, or the current induced in the second set of one or more coils. The processing unit may be integral to the receiving or transmitting sensor, may be implemented in a separate computing device, or distributed across any combination of the receiving sensor, transmitting sensor and/or optional separate computing device.

FIG. 1 shows a diagram of a system for sensing bend (e.g. bending) angles through magnetic field coupling in accordance with an example. In one aspect, the system includes an electromagnetic transmitting sensor 110, an electromagnetic receiving sensor 120, and one or more processing units 130 coupled to the transmitting sensor 110 and the receiving sensors 120. The one or more processing units 130 may be implemented in the transmitting sensor 110, the receiving sensor 120, a separate device, or distributed across any combination thereof. Depending upon the control functions and/or data processing functions performed by the processing units in the transmitting sensor 110, the receiving sensor 120 and/or separate device, the one or more processing units may be implemented by a combinational logic circuit, a field programmable gate array (FPGA), an application specific integrated circuit (ASIC), a microcontroller, a mobile processor, a digital signal processor (DSP), and/or a central processing unit (CPU).

The transmitting sensor 110 can be configured to be disposed on or about a first body segment, and the electromagnetic receiving sensor 120 can be configured to be disposed on or about a second body segment. For example, the transmitting sensor 110 can be disposed about a forearm 140 of an individual, and the electromagnetic receiving sensor 120 can be disposed about the corresponding arm 150 of the individual. In another example, the transmitting sensor 110 can be disposed about a thigh, and the electromagnetic receiving sensor 120 can be disposed about the calf or ankle 150 of the individual.

In one aspect, the transmitting sensor 110 can be configured to transmit a magnetic field, and the electromagnetic receiving sensor 120 can be configured to receive a portion of the magnetic field transmitted from the transmitting sensor 110 that couples to the electromagnetic receiving sensor 120.

In one aspect, the one or more processing units 130 can be configured to capture data related to the magnetic field coupling between the transmitting sensor 110 and the receiving sensor 120. In one aspect, the one or more processing units 130 can also determine an angular displacement as a function of the captured data. The angular displacement between a first and second body segment can be determined in real time from the magnetic field coupling data.

Figure 2A:
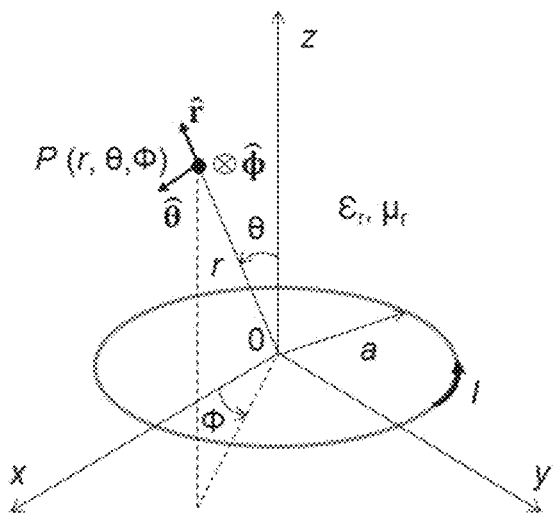
FIGS. 2A and 2B are diagrams illustrating a magnetic field generated by a transmitting loop and the magnetic field coupled to a receiving loop in accordance with an example embodiment.

The system for sensing bending angles through magnetic field coupling can achieve a high resolution and wide range of bending angle measurements. To illustrate the range and resolution, the following exemplary simulation analysis is provided. In one aspect, the electromagnetic field for a small conducting loop of uniform current I situated in a linear, homogeneous medium of relative permittivity $\varepsilon_r$ and permeability $\mu_r$ can be illustrated in FIG. 2A. An electrical small loop is a valid assumption because the system for sensing bending angles through magnetic field coupling can operate in a low radio frequency (RF) range, for example up to 100 mega Hertz (MHz). The dimension of the loop can therefore be less than about a tenth of the wavelength. The electric field E and the magnetic field H of the loop in space at any point can be defined by (r, θ, φ) in a spherical coordinate system as:

$$E_\phi = \hat{\mathbf{?}} - \frac{IS}{4\pi} j\beta \left(1 + \frac{1}{j\beta r}\right) \frac{e^{-j\beta r}}{r} \sin(\theta)\hat{\phi} \quad (1)$$

$$H_\theta = \hat{\mathbf{?}} \frac{IS}{4\pi} j\omega\varepsilon \left(1 + \frac{1}{j\beta r} + \frac{1}{(j\beta r)^2}\right) \frac{e^{-j\beta r}}{r} \sin(\theta)\hat{\theta} \quad (2)$$

$$H_r = \hat{\mathbf{?}} \frac{IS}{2\pi} j\omega\varepsilon \left(\frac{1}{j\beta r} + \frac{1}{(j\beta r)^2}\right) \frac{e^{-j\beta r}}{r} \cos(\theta)\hat{r} \quad (3)$$

where $S=\pi a^2$ is the surface of the loop with radius a, β is the phase coefficient of the propagating wave, and $\omega=2\pi f$ is the angular frequency (f is the operating frequency of the electromagnetic transmitting and receiving sensors). Equations 1-3 are valid at any point P(r, θ, φ) where r is the radial distance from the source to the point P, θ is the elevation angle (0≤θ≤180°) and φ is the azimuth angle (0≤φ≤360°) as depicted in FIG. 2A. Note that all vectors quantities are expressed in bold up-right designators.

Figure 2B:
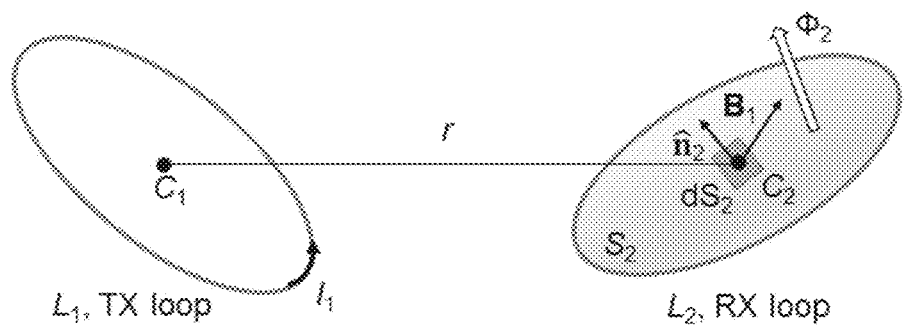

Considering two conducting loops $L_1$ and $L_2$ in a linear, homogeneous medium and assuming that loop $L_1$ has induced current $I_1$, as illustrated in FIG. 2B, $L_1$ acts as a transmitting loop and $L_2$ acts as a receiving loop. The magnetic field due to the first loop, $H_1$, or magnetic flux density vector $B_1$ ($B_1=\mu H_1$), is produced everywhere. Some of the field lines are coupled through $L_2$. The total flux of the magnetic field through loop $L_2$ due to the current $I_1$ can be expresses as:

$$\Phi_2 = \hat{\mathbf{?}} \int_{S_2} B_1 \cdot dS_2 \quad (4)$$

The intensity of the measured signal at the transmitting loop RX depends on the relative orientation of the transmitting and receiving loops as well as the distance between them.

Figure 3:
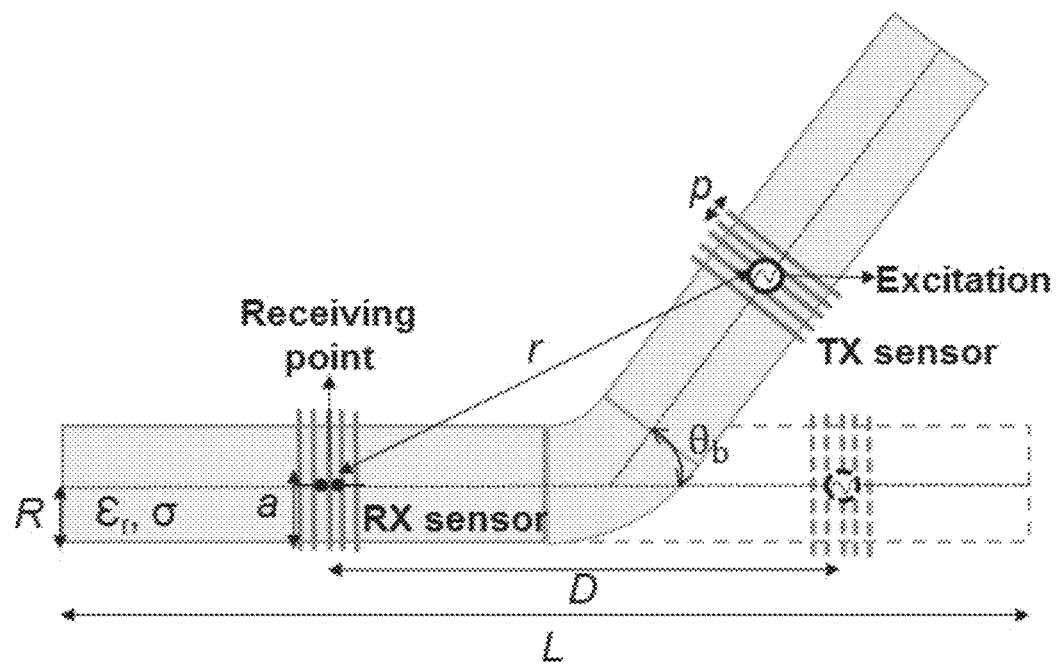
FIG. 3 is a diagram illustrating sensing of bending angles through magnetic field coupling in accordance with an example embodiment.
Figure 4:
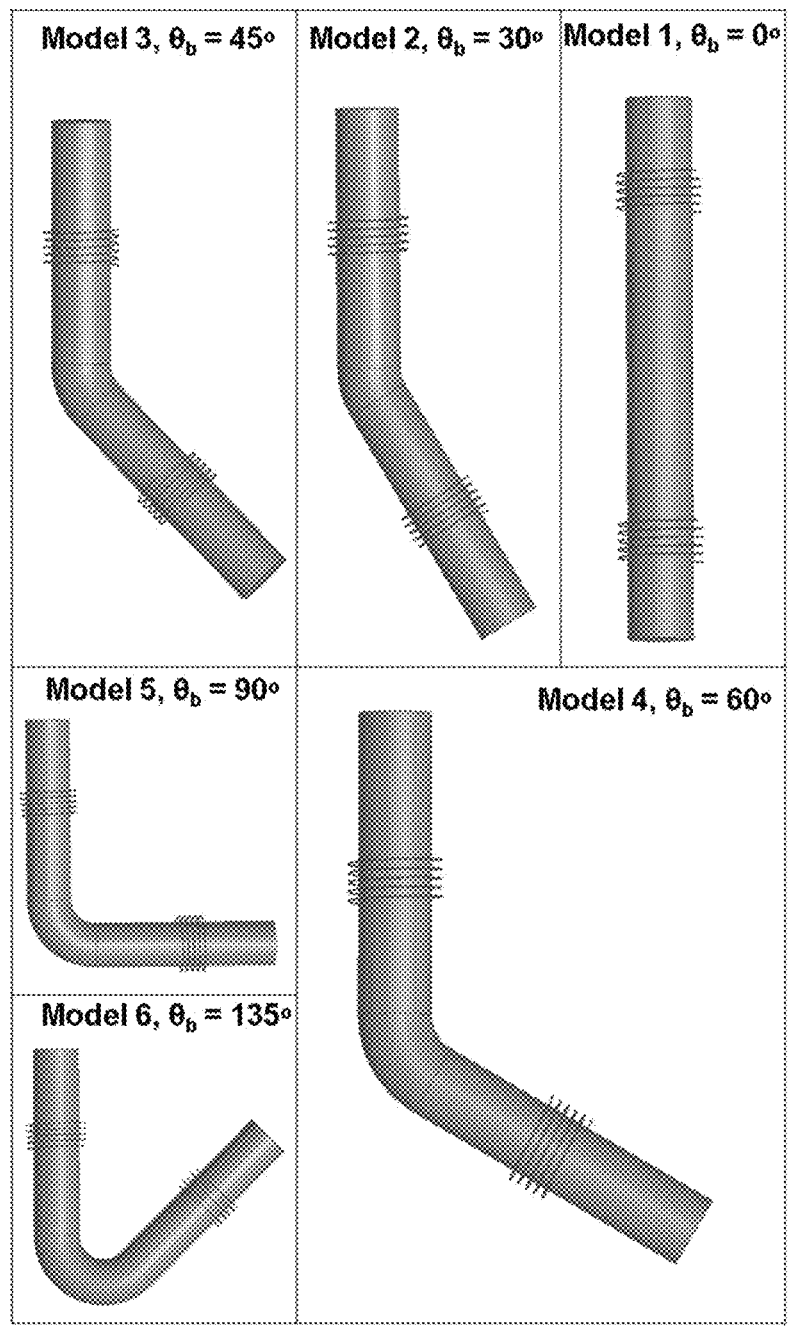
FIG. 4 is a diagram illustrating six exemplary bending angle models in accordance with an example embodiment.

FIG. 3 illustrates sensing of bending angles through magnetic field coupling in accordance with an example. In one aspect, the bending angle can for example be sensed by electromagnetic transmitting and receiving sensors wrapped around the arm and forearm of a subject. The bending angle $\theta_b$ can be defined with respect to a horizontal plane and the radial distance r between the excitation point and the receiving point. The human arm, can be for example, be modeled as a cylinder of circular cross section. Although, electromagnetic field propagation in human tissues is frequency dependent, the human arm can be approximated as a muscle-equivalent of relative permittivity of $\varepsilon_r=77$, permeability of $\mu_r=1$, and conductivity of $\sigma=0.67$ S/m. In order to improve the level of transmitted signal, electromagnetic transmitting and receiving sensors including five turns of coils can be used. To mimic different bending angles of the human arm wearing electromagnetic transmitting and receiving sensors, for example, six numerical models, as illustrated in FIG. 4, can be analyzed. The six numerical models can include bending angles of 0°, 30°, 45°, 60°, 90°, and 135°. The simulation parameters are given in Table 1.

TABLE 1

| Parameter | Value | Description |
|---|---|---|
| f | 10 to 100 MHz | Frequency |
| a | 5 cm | Coil Radius |
| p | 1 cm | Coil pitch |
| n | 5 | Number of coil turns |
| R | 4 cm | Arm radius |
| L | 65 cm | Arm length |
| D | 42 cm | TX-RX coil distance |
| $\theta_b$ | 0°, 30°, 45°, 60°, 90°, and 135° | Bending angle |
| $\varepsilon_r$ | 77 | Relative permittivity of the arm |
| σ | 0.67 S/m | Conductivity |

Figure 5:
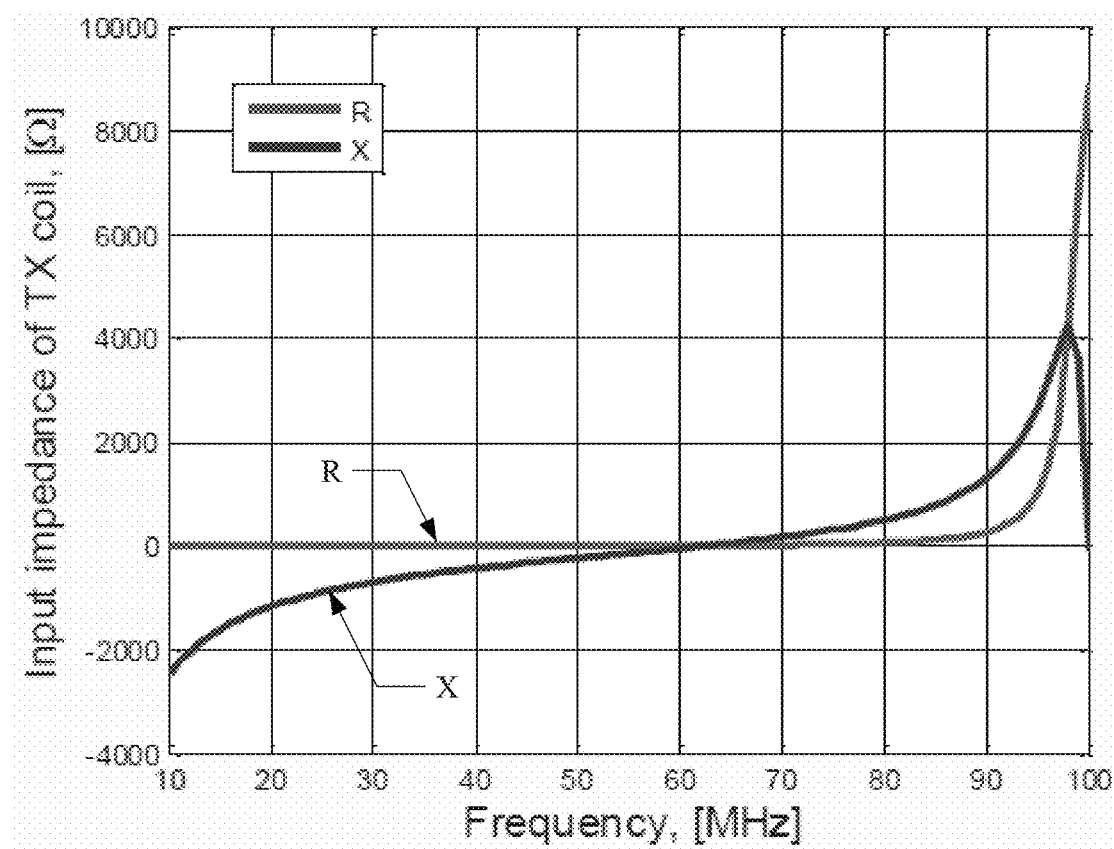
FIG. 5 is a diagram illustrating an exemplary input impedance of the coil as a function of frequency in accordance with an example embodiment.
Figure 6A:
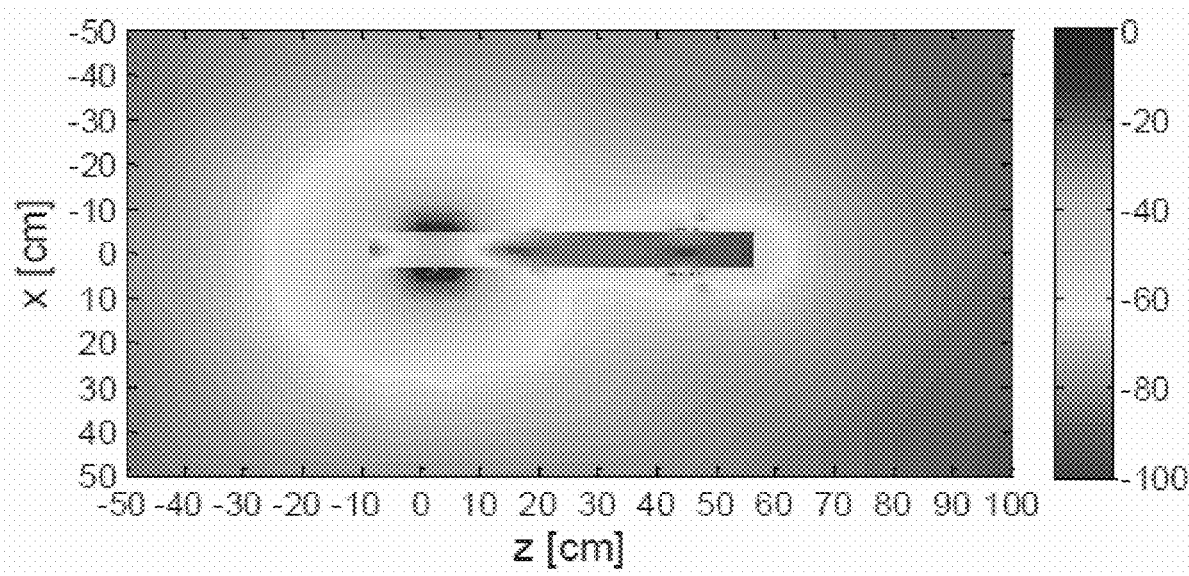
FIGS. 6A and 6B are diagrams illustrating a 2D electric and magnetic field distribution, respectively, inside an exemplary simulation phantom and surrounding medium, in accordance with an example embodiment.
Figure 6B:
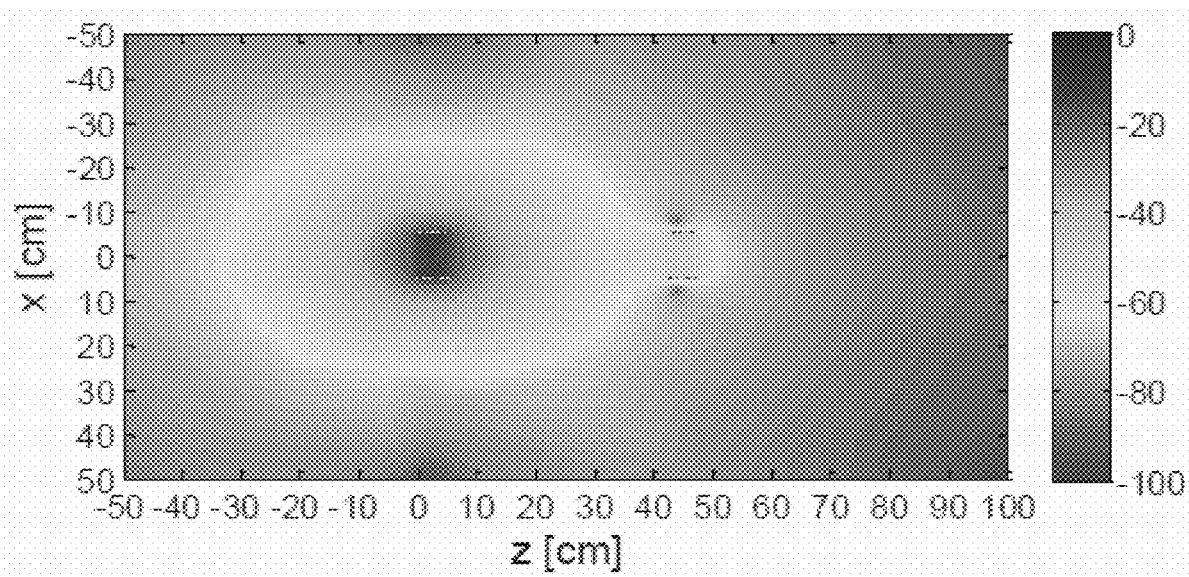

FIG. 5 shows an exemplary input impedance of the electromagnetic transmitting coil TX for model 1, $\theta_b=0°$, D=42 cm. From the graph of the input impedance, the self-resonant frequency fr of the exemplary simulation is approximately 62 MHz. FIGS. 6A and 6B shows a two-dimensional (2D) electric and magnetic field distribution inside the exemplary human muscle equivalent simulation phantom and in the surrounding medium (e.g., air) at the self-resonant frequency. Because the maximum distance the electromagnetic wave propagates in the system from transmitter to receiver, D=42, is much smaller than the free space wavelength (λ=480 cm), most of the signal is transmitted in the near-field region. In addition, the magnetic field is more dominant due to the stronger near field term $1/r^3$ (e.g., Equations 2 and 3), than the electric filed (e.g., Equation 1). FIGS. 6A and 6B illustrates that the magnetic field is not affected by the dielectric properties of human tissue as opposed to the electric field.

Figure 7A:
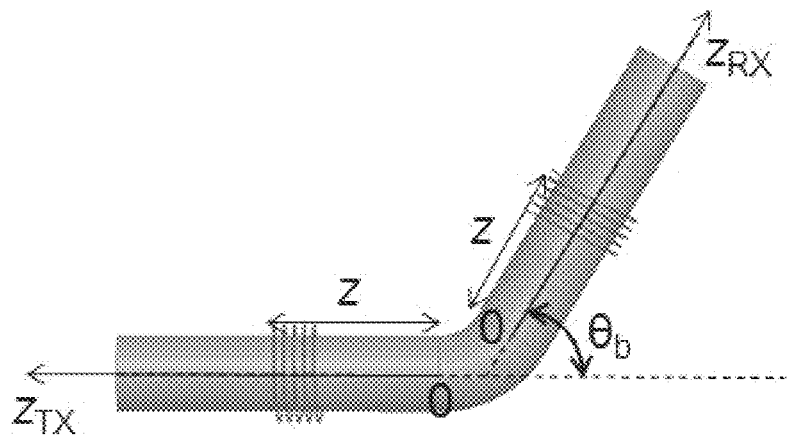
FIGS. 7A and 7B are diagrams illustrating two different arrangements of the transmitting and receiving coil relative to the exemplary simulation phantom in accordance with an example embodiment.
Figure 7B:
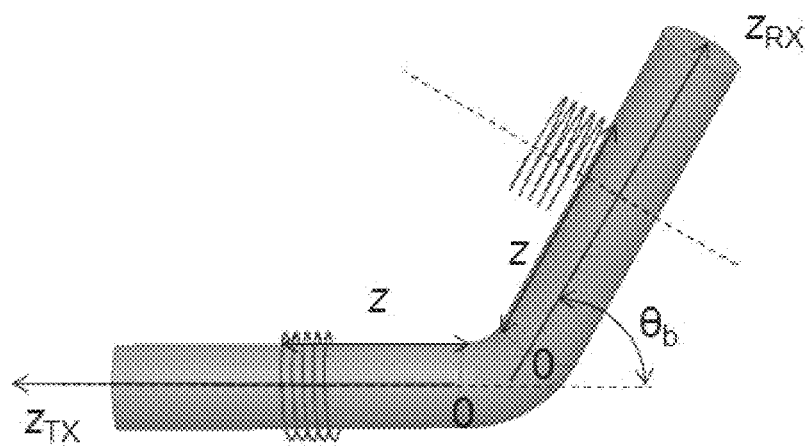
Figure 8A:
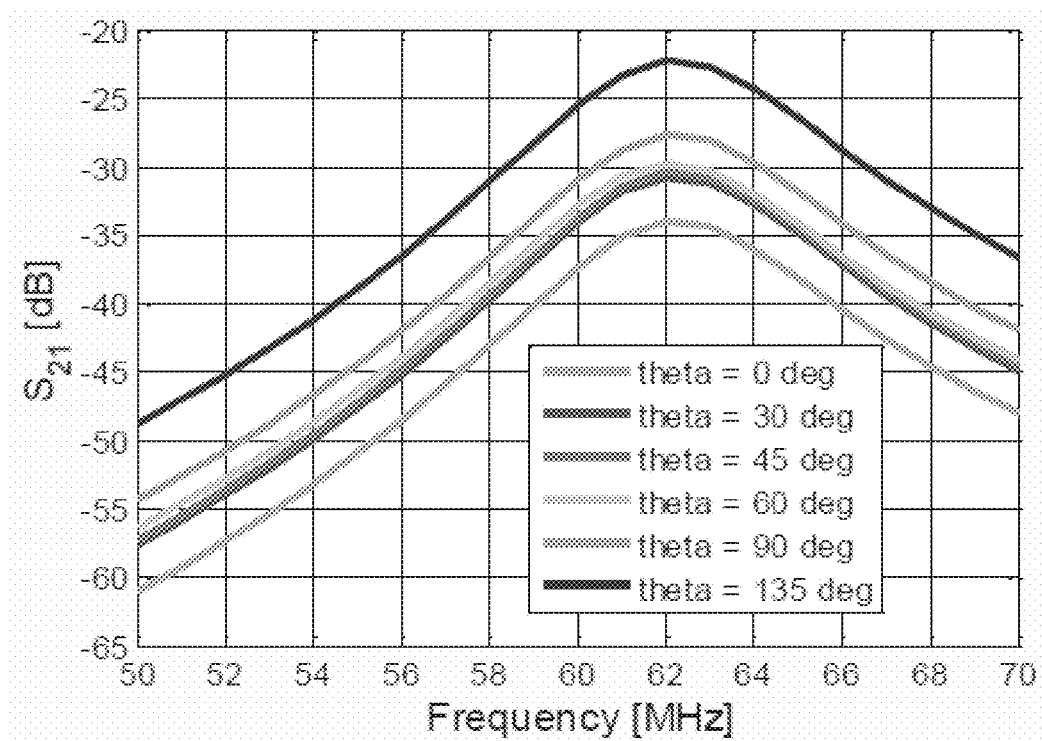
FIGS. 8A and 8B are diagrams illustrating the transmission parameter as a function of frequency for the two-different transmitting and receiving coil arrangements for the exemplary simulation in accordance with an example embodiment.
Figure 8B:
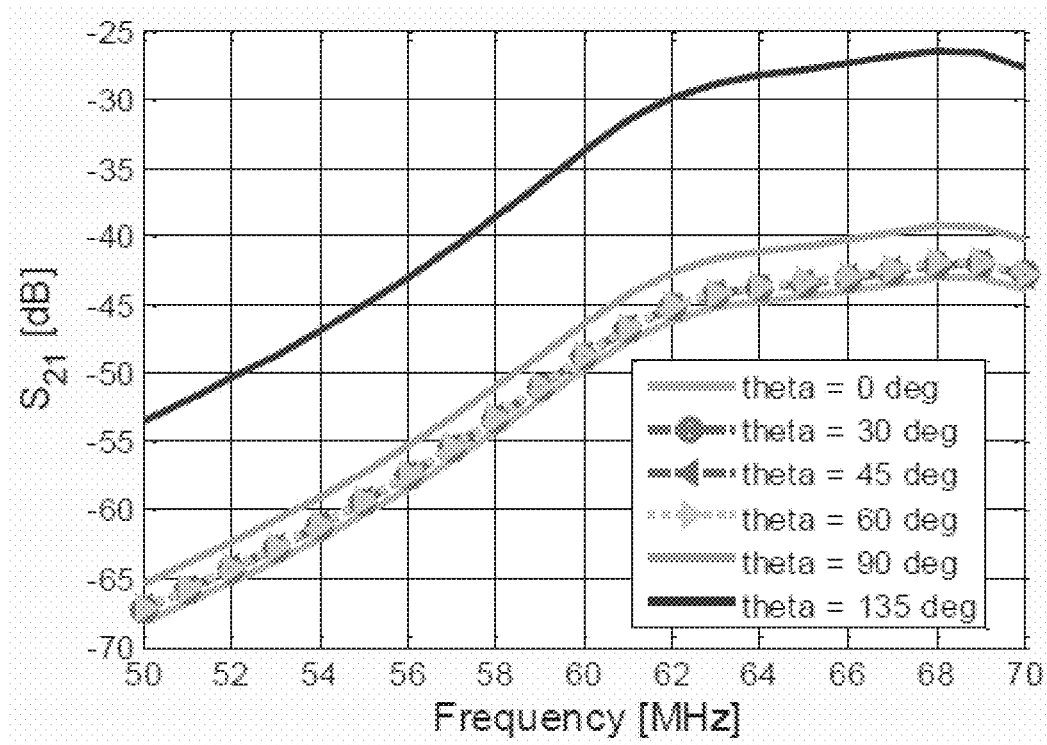
Figure 9:
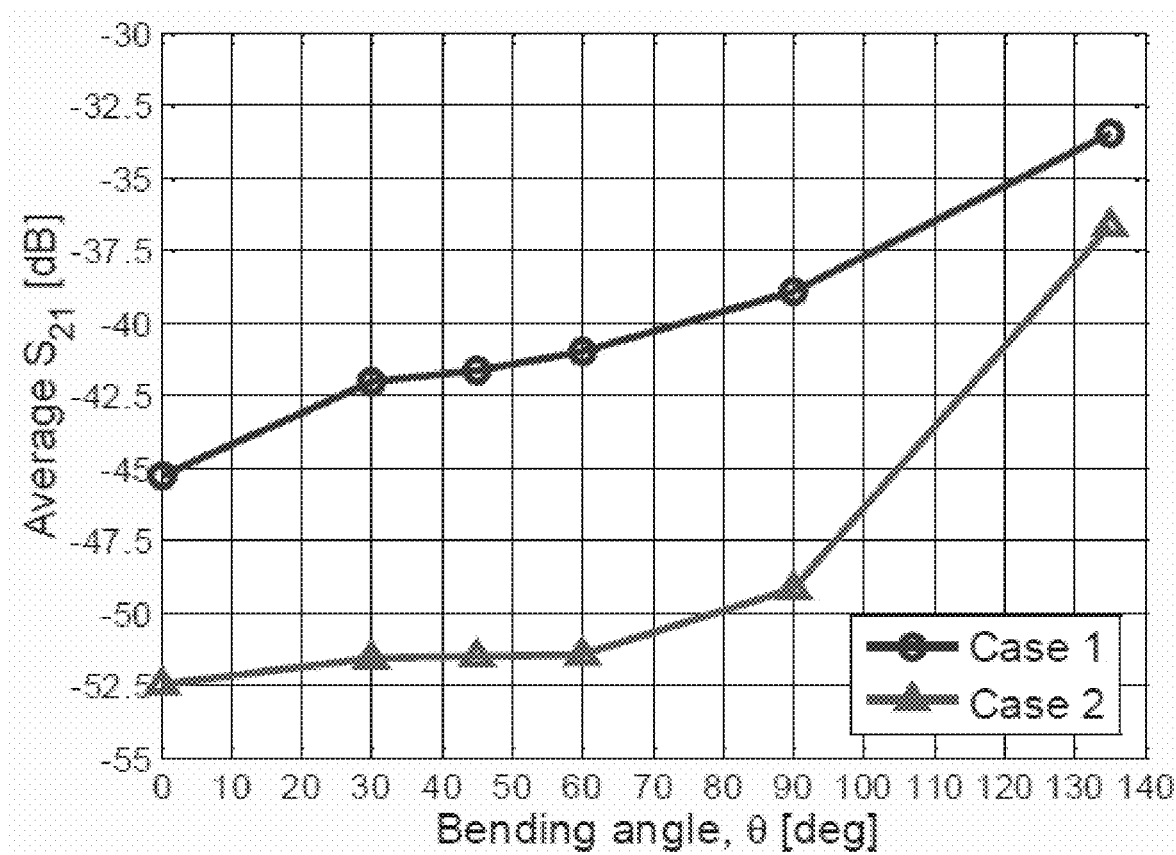
FIG. 9 is a diagram illustrating the average transmission parameter for the exemplary simulation in accordance with an example embodiment.

The transmission parameter $S_{21}$, as measured for the signal level at the receiving coil RX, can be analyzed for two different cases as illustrated in FIGS. 7A and 7B. The transmission parameter can be analyzed for the case where the transmitting coil TX and the receiving coil RX coincide with the longitudinal axis of the simulation phantom, and for the case where the axis of the receiving coil RX is orthogonal to the axis of the simulation phantom. In both cases the transmission and receiving coils TX, RX can be at a fixed distance Z=15 cm, wherein z is defined with respect to a local coordinate system associated with the coils. The results of both analyses the transmission parameter $S_{21}$ as a function of frequency for both cases are illustrated in FIGS. 8A and 8B, respectively. FIG. 9 indicates an average transmission parameter $S_{21}$, over twenty frequency points, at six bending angles of 0°, 30°, 45°, 60°, 90°, and 135°, for both cases. The change in the average transmission parameter $S_{21}$, between successive bending angle positions is tabulated in Table 2.

TABLE 2

| Averaged $\Delta S_{21}$ | Coincident Coils | Orthogonal Coils |
|---|---|---|
| $S_{21, \theta=135°} - S_{21, \theta=90°}$ | 5.45 | 12.51 |
| $S_{21, \theta=90°} - S_{21, \theta=60°}$ | 2.09 | 2.29 |
| $S_{21, \theta=60°} - S_{21, \theta=45°}$ | 0.65 | 0.056 |
| $S_{21, \theta=45°} - S_{21, \theta=30°}$ | 0.41 | 0.11 |
| $S_{21, \theta=30°} - S_{21, \theta=0°}$ | 3.27 | 0.91 |

Accordingly, the transmission parameter signal monotonically increases with increasing bending angle. However, for bending angles of less than 60° changing in 15° increments, the change in the transmission parameter signal is relatively small (e.g., $\Delta S_{21} < 1$ dB).

Figure 10A:
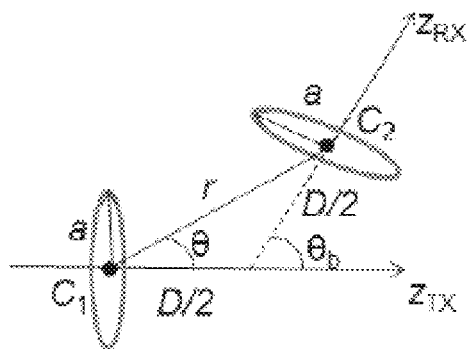
FIGS. 10A and 10B are diagrams illustrating two different arrangements of the transmitting and receiving coil of the simplified simulation in accordance with an example embodiment.
Figure 10B:
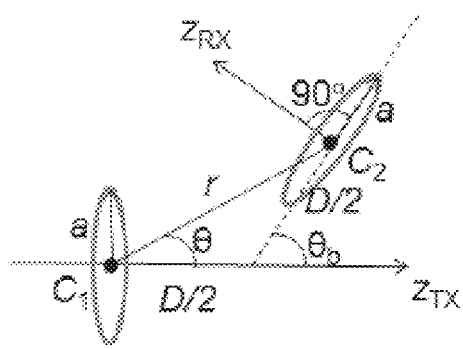

Based on Equations 2 and 3 and using a near-field assumption ($\beta \ll 1$), normalized magnitudes of the $\theta$-component and the r-component of the magnetic field can be written as:

$$|H_\theta^{norm}| = \boxed{?}\frac{|H_\theta|}{C_1} = \boxed{?}\frac{1}{2}\left|\frac{1}{\beta r^2} - j\frac{1}{\beta^2 r^3}\right| |\sin\boxed{?}(\theta)| \quad (5)$$

$$|H_r^{norm}| = \boxed{?}\frac{|H_r|}{C_1} = \boxed{?}\left|\frac{1}{\beta r^2} - j\frac{1}{\beta^2 r^3}\right| |\cos\boxed{?}(\theta)| \quad (6)$$

wherein the normalization constant is $C_1 = \omega \epsilon IS/(2\pi)$. In addition, for the purpose of this calculation, in order to use analytic expressions (e.g., Equations 2 and 3), the 3D simulation models in FIGS. 7A and 7B were simplified assuming transmitting and receiving coils TX, RX as single-turn coils, of radius a, located in free space (e.g., the simulation phantom removed). The simplified models are illustrated in FIGS. 10A and 10B. In FIG. 10A the axis of the transmitting and receiving coils TX, RX coincide with the longitudinal axis of the removed simulation phantom. In FIG. 10B the receiving coil RX is orthogonal to the axis of the removed simulation phantom. The elevation angle $\theta$ and radial distance r between the transmitting and receiving coils TX, RX, in FIGS. 10A and 10B, can be expressed in terms of bending angle $\theta_b$ as:

$$\theta = \boxed{?}\frac{\theta_b}{2} \quad (7)$$

$$r = D\cos\left(\frac{\theta_b}{2}\right) \quad (8)$$

Substituting the relationships in Equations 7 and 8 into Equations 5 and 6, the magnetic field as a function of $\theta_b$ can be obtained. The normalized magnetic field $1/r^2$ and $1/r^3$ terms of the radial component as a function of $\theta_b$ can be illustrated in FIG. 11. The magnetic field intensity exhibits similar monotonic behavior with increasing bending angle as was indicated for the exemplary transmission parameter $S_{21}$ illustrated in FIG. 9.

Figure 11:
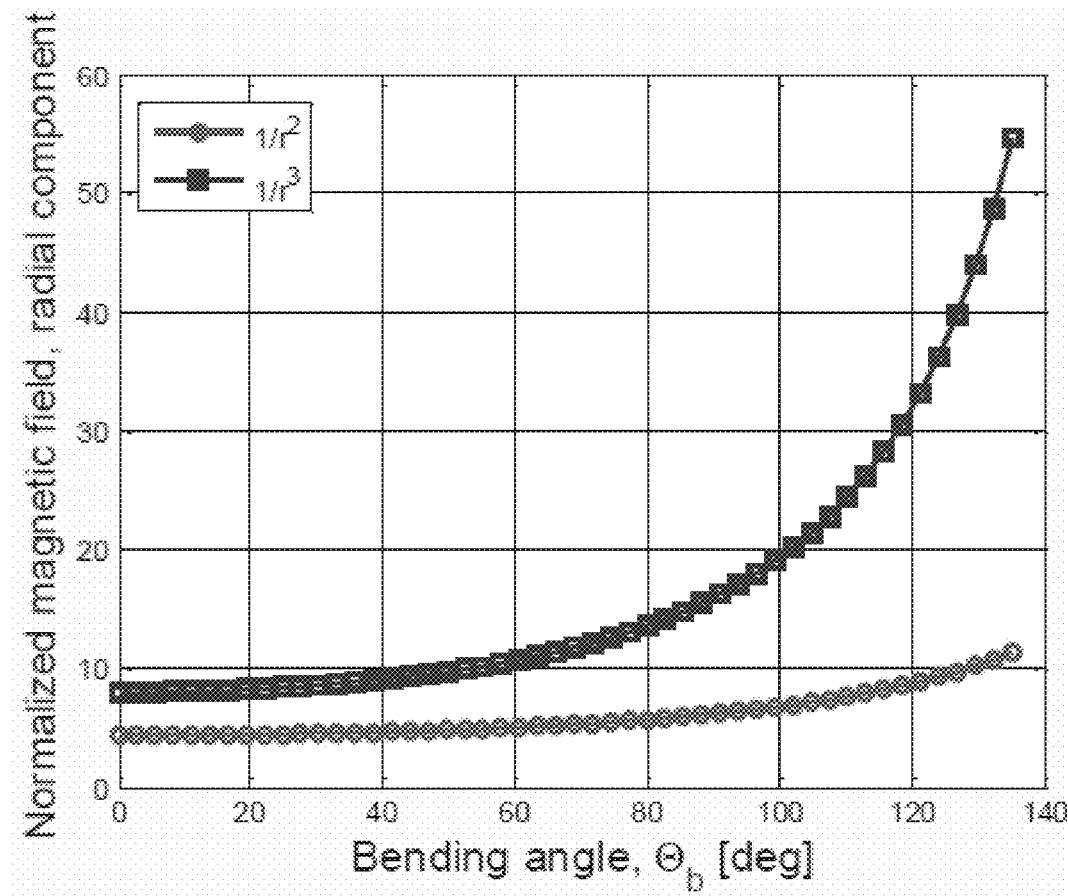
FIG. 11 is a diagram illustrating the normalized magnetic field as a function of the bending angle in accordance with an example embodiment.

The total magnetic flux passing through the receiving coil RX, for the cases illustrated in FIGS. 10A and 10B can be calculated as a function of the bending angle. Assuming that the loops of the receiving coil RX are electrically and spatially small (e.g., the loop radius is much smaller than the radial distance connecting the feeding point of the transmitting and receiving coils TX, RX (a$\ll\lambda$ and a$\ll$r), Equation 4 can be approximated as:

$$\Phi_2 \approx B_1 \cdot S_2 = B_{r1} \cdot S_2 + B_{\theta 1} \cdot S_2 \quad (9)$$

where $B_{r1}$ and $B_{\theta 1}$ are magnetic flux density components due to induced current in the loop of the transmitting coil TX computed at the center of the loop of the receiving coil RX. The components can be calculated by substituting the relationships of Equation 7 and 8 into Equations 5 and 6, and applying the relationship $B=\mu H$. In addition, only the stronger term, $1/r^3$, as shown in FIG. 11, is taken into account. In accordance with these assumption, the normalized total magnetic flux passing through the receiving coil in the cases illustrated in FIGS. 10A and 10B can be calculated as:

$$\Phi_{2,case1}^{norm} = \boxed{?}\frac{|\Phi_{2,case1}|}{C_2} = \boxed{?}\frac{1}{\cos\left(\frac{\theta_b}{2}\right)}\left(1 + \frac{1}{2}\tan^2\left(\frac{\theta_b}{2}\right)\right) \quad (10)$$

$$\Phi_{2,case2}^{norm} = \boxed{?}\frac{|\Phi_{2,case2}|}{c_2} = \boxed{?}\frac{1}{4}\frac{\sin\theta_b}{\cos^3\left(\frac{\theta_b}{2}\right)} \quad (11)$$

wherein the normalized constant is $C_2 = \mu\pi a^2/D^3$. The normalized total magnetic flux for the two cases in FIGS. 9A and 9B are illustrated in FIG. 12.

Figure 12:
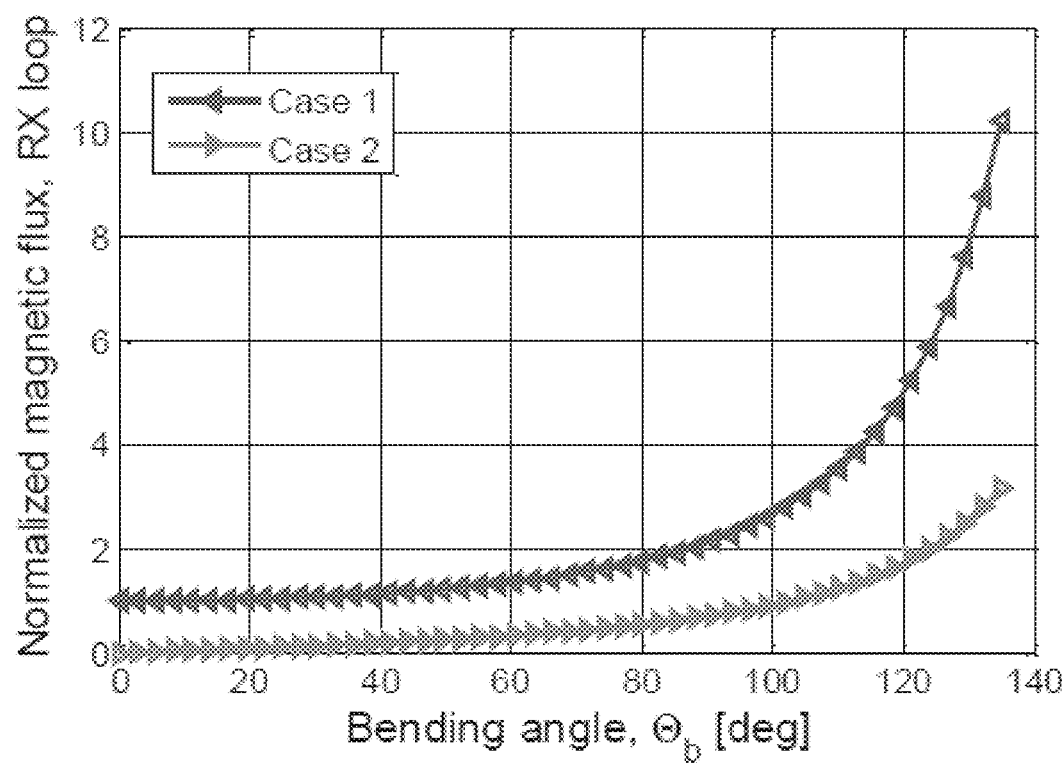
FIG. 12 is a diagram illustrating the normalized magnetic flux as a function of the bending angle in accordance with an example embodiment.

Quantitative comparison of numerical results, as illustrated in FIG. 9 and analytic estimates, as illustrated in FIG. 12, show a similar nonlinear monotonic trend with increases in the bending angle of the body part. In accordance with the data, better signal resolution is achieved for higher bending angles. Although the two sets of results are of different nature, their comparison is valid because both signals are proportional to the magnetic field. However, these signals may not be readily compared quantitatively because they are computed based on different sensor designs.

In one aspect, coil parameters such as size, number of turns, pitch, and wire radius can be optimized to achieve a particular performance at a self-resonant frequency. Also, the resonance of the system can be controlled by loading each coil with appropriately chosen capacitance values. In addition, the path loss can be improved by adding extra passive coils between the transmitting and receiving coils TX, RX.

Figure 13:
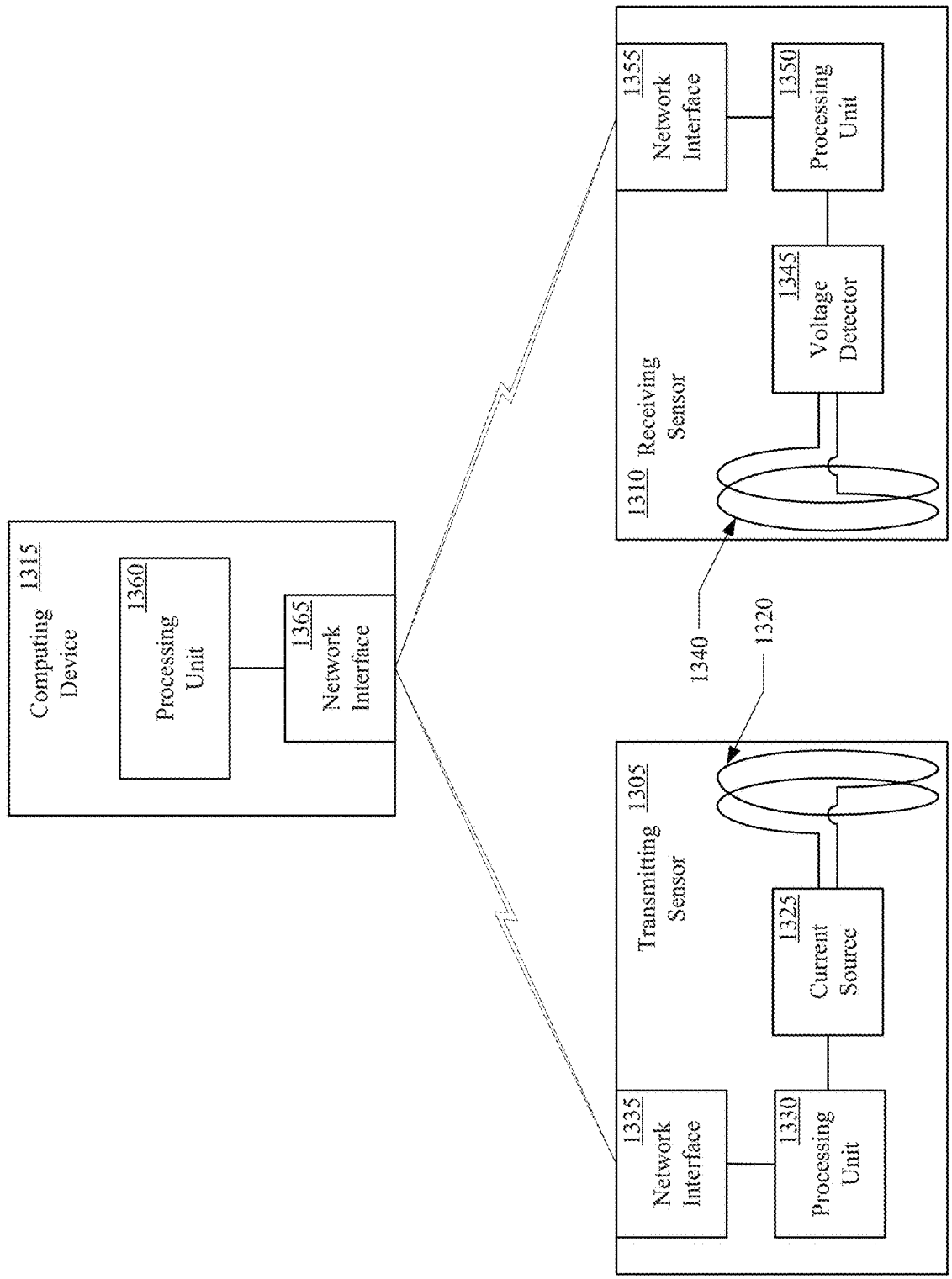
FIG. 13 is a diagram of a system for sensing bending angles through magnetic field coupling in accordance with another example embodiment.

In view of the concepts from the above discussed simulation, additional embodiments of the present technology will be further described. FIG. 13 is a diagram of a system for sensing bending angles through magnetic field coupling in accordance with another example. In one aspect, the system includes an electromagnetic transmitting sensor 1305, an electromagnetic receiving sensor 1310, and a computing device 1315. The transmitting sensor 1305 can be configured to be disposed about a first body segment, and the electromagnetic receiving sensor 1310 can be configured to be disposed about a second body segment. In one aspect, the transmitting sensor 1305 can be included in a first form factor, and the electromagnetic receiving sensor 1310 can be included in a second form factor. The first and second form factors can be, for example, a wrist band and an arm band, a watch and an arm band, a bracelet and an arm band. Other possible form factors may include a ring, a leg band, an anklet, a belt, a necklace, a choker, an earring, and a headband.

In one aspect, the transmitting sensor 1305 can include one or more coils 1320, a current source 1325, a processing unit 1330, and a network interface 1335. A current, generated by the current source 1325, flowing through the one or more coils 1325 generates a magnetic field that radiates from the one or more coils 1325. The processing unit 1330 may control the amplitude, frequency, duty cycle and other applicable parameters of the current generated by the current source 1325, thereby controlling the magnetic field flux, duty cycle, and other applicable parameters of the magnetic field radiated from the one or more coils 1320. In one example, the processing unit 1330 of the transmitting sensor 1305 may perform substantially control functions, and therefore may be implemented in combinational logic circuit, a field programmable gate array (FPGA), an application specific integrated circuit (ASIC), or a microcontroller. The network interface 1335 of the transmitting sensor 1305 and the network interface 1365 of the computing device 1315 can operate to transfer data, instructions, control signals and the like between the processing unit 1360 of the computing device 1315 and the processing unit 1330 of the transmitting sensor 1305 to control the magnetic field flux, duty cycle, and other applicable parameters of the magnetic field generated by the transmitting sensor 1305.

In one aspect, the receiving sensor 1310 can include one or more coils 1340, a voltage detector 1345, a processing unit 1350, and a network interface 1355. A portion of the magnetic field transmitted from one or more coils 1320 of the transmitting sensor 1305 couples to the one or more coils 1340 of the electromagnetic receiving sensor 1320. The voltage detector 1345 can determine the open circuit voltage induced in the one or more coils 1340 by the portion of the magnetic field that couples to the one or more coils 1340. The processing unit 1350 can be configured to acquire data related to the magnetic field coupling between the one or more coils 1325 of the transmitting sensor 1305 and the one or more coils 1340 of the receiving sensor 1310 from the open circuit voltage detected by the voltage detector 1345. Alternatively, the receiving sensor 1310 can include a current detector instead of a voltage detector 1345. The current detector can determine the current induced in the one or more coils 1340 by the portion of the magnetic field that couple to the one or more coils 1340. The processing unit 1350 can be configured to acquire data related to the magnetic field coupling between the one or more coils 1325 of the transmitting sensor 1305 and the one or more coils 1340 of the receiving sensor 1310 from the current detected by the current detector. In one example, the processing unit 1350 of the receiving sensor 1310 may perform substantially control functions, and therefore may be implemented in combinational logic circuit, a field programmable gate array (FPGA), an application specific integrated circuit (ASIC), or a microcontroller. The network interface 1355 of the receiving sensor 1310 and the network interface 1365 of the computing device 1315 can transfer data, instructions, control signals and the like between the processing unit 1330 of the receiving sensor 1310 and the processing unit 1360 of the computing device 1315 related to the magnetic field coupling between the transmitting sensor 1305 and the electromagnetic receiving sensor 1310.

In one aspect, the processing unit 1360 of the computing device 1315 can control the magnetic field generated by the transmitting sensor 1305 and the sensing of the magnetic field coupling by the electromagnetic receiving sensor 1310. The processing unit 1360 can also determine an angular displacement as a function of the determined magnetic field coupling. In one example, the processing unit 1360 of the computing device 1315 may perform both control functions and data processing, and therefore may be implemented in an application specific integrated circuit (ASIC), a microcontroller, a mobile processor, a digital signal processor (DSP), and a central processing unit (CPU).

In one aspect, the radius of the set of one or more coils 1320, 1340 of the transmitting and receiving sensors 1305, 1310 can be less than a distance between the sets of one or more coils 1320, 1340. Furthermore, the distance between the transmitting and receiving sensors 1305, 1310 will typically be between 1 cm and 200 cm, therefore the current driven through the one or more coils 1320 of the transmitting sensor 1305 may be relatively small, thereby consuming relatively low amounts of power. In addition, the power needed to communicate between the network interfaces 1335, 1355, 1365 of the transmitting sensor 1305, the receiving sensor 1310 and the computing device 1315 will also be typically relatively low. In addition, the processes of generating the magnetic field at the transmitting sensor 1305, determining the magnetic field coupling at the receiving sensor 1310 and determining the angular displacement by the computing device 1315 may be performed periodically, instead of continuously, to further conserve power.

In one aspect, the network interfaces 1335, 1355, 1365 of the transmitting sensor 1305, the receiving sensor 1310, and computing device 1315 can comprise a Body Area Network (BAN), or a part thereof. The BAN can provide for Human Body Communication (HBC) including communication of the determined angular displacement between body segments to a user or one or more other computing devices.

As illustrated in the example of FIG. 13, the processing units 1330, 1350 of the transmitting sensor 1305 and receiving sensor 1310 can provide for such functions and data buffering, analog-to-digital conversion, and digital-to-analog conversion. The majority of the processing can be offloaded from the transmitting sensor 1305 and the receiving sensor 1310 to be performed by the processing unit 1360 of a separate computing device, such as a smart phone, tablet computer, laptop computer, desktop computer, remote server computer or similar computing device. Accordingly, the control and processing functions of the system for sensing bending angles are distributed across the processing unit 1330 of the transmitting sensor 1305, the processing unit 1350 of the receiving sensor 1310 and the processing unit 1360 of the computing device.

Figure 14:
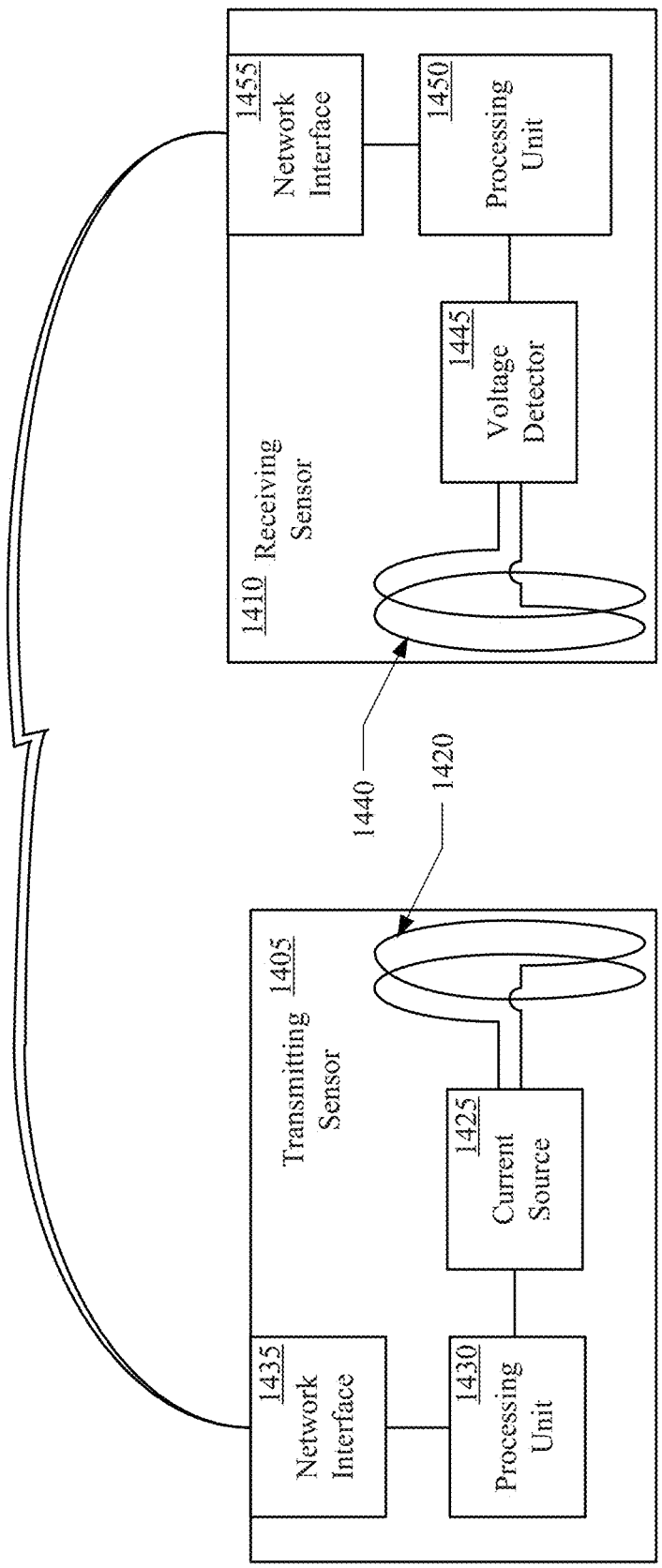
FIG. 14 is a diagram of a system for sensing bending angles through magnetic field coupling in accordance with another example embodiment.

FIG. 14 is a diagram of a system for sensing bending angles through magnetic field coupling in accordance with another example. The one or more coils 1420, the current source 1425, the processing unit 1430 and the network interface 1435 of the electromagnetic transmitting sensor 1405 are substantially similar to the electromagnetic transmitting sensor 1305 as described above with reference to FIG. 13. Likewise, the one or more coils 1440, the voltage or current detector 1445 and network interface 1455 of the electromagnetic receiving sensor 1410 are substantially similar to the electromagnetic receiving sensor 1310 as described above with reference to FIG. 13.

In one aspect, the electromagnetic receiving sensor 1410 includes a processing unit 1450. The network interface 1435 of the transmitting sensor 1405 and the network interface 1455 of the electromagnetic receiving sensor 1410 can operate to transfer data, instructions, control signals and the like between the processing unit 1450 of the electromagnetic receiving sensor 1410 and the processing unit 1430 of the transmitting sensor 1405 to control the magnetic field flux, duty cycle and other applicable parameters of the magnetic field generated by the transmitting sensor 1405. The processing unit 1450 of the electromagnetic receiving sensor 1410 can also control sensing of the magnetic field coupling by the electromagnetic receiving sensor 1410. The processing unit 1450 can also determine an angular displacement as a function of the determined magnetic field coupling. In one example, the processing unit 1450 of the receiving sensor 1410 may perform both control functions and data processing, and therefore may be implemented in an application specific integrated circuit (ASIC), a microcontroller, a mobile processor, a digital signal processor (DSP), and a central processing unit (CPU).

In one aspect, the network interfaces 1435, 1455 of the transmitting sensor 1405 and receiving sensor 1410 can comprise a Body Area Network (BAN), or a part thereof. The BAN can provide for Human Body Communication (HBC) including communication of the determined angular displacement between body segments to a user or one or more other computing devices.

In one aspect, the radius of the set of one or more coils 1420, 1440 of the transmitting and receiving sensors 1405, 1410 can be less than a distance between the sets of one or more coils 1420, 1440. Furthermore, the distance between the transmitting and receiving sensors 1405, 1410 will typically be between 1 cm and 200 cm, therefore the current driven through the one or more coils 1420 of the transmitting sensor 1405 may be relatively small, thereby consuming relatively low amounts of power. In addition, the power needed to communicate between the network interfaces 1435, 1455 of the transmitting and receiving sensors 1405, 1410 will also be typically relatively low. In addition, the processes of generating the magnetic field at the transmitting sensor 1405, determining the magnetic field coupling and determining the angular displacement at the receiving sensor 1410 may be performed periodically, instead of continuously, to further conserve power.

As illustrated in the example of FIG. 14, the processing can be performed by the processing unit 1450 of the electromagnetic receiving sensor 1410. In such case, the electromagnetic receiving sensor 1410 can be a dedicated device with the needed data processing integrated therein. In other instance, the electromagnetic receiving sensor 1410 can be integrated into an electronic device such as a smart watch or other device that can provide the data processing function of the electromagnetic receiving sensor 1410. Accordingly, the control and processing functions of the system for sensing bending angles can be distributed across the processing unit 1430 of the transmitting sensor 1405, and the processing unit 1450 of the receiving sensor 1410. In another example, the processing can be performed by the control and data processing unit of the electromagnetic transmitting sensor.

Figure 15:
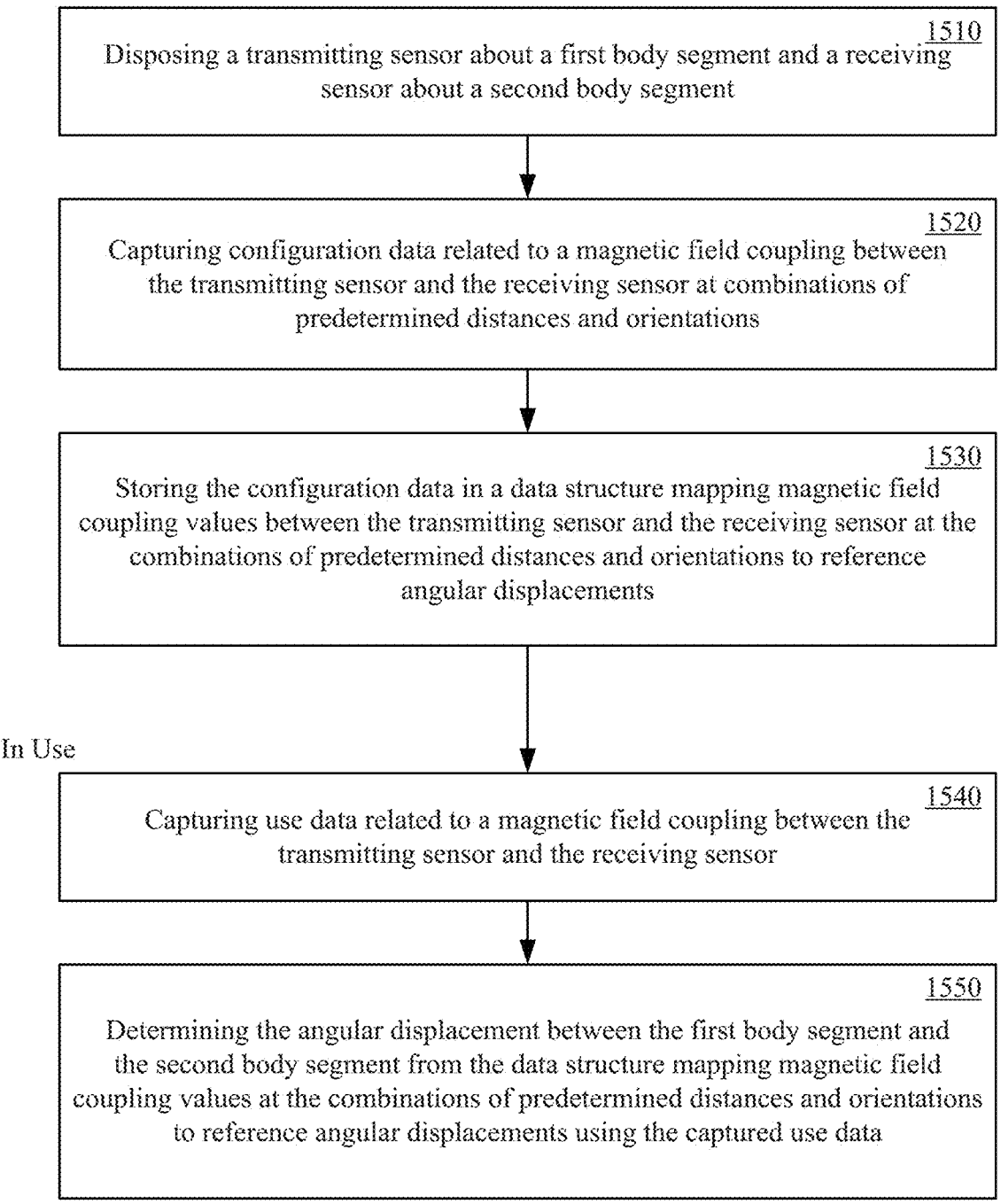
FIG. 15 is a diagram of a method for sensing bending angles through magnetic field coupling in accordance with an example embodiment.

FIG. 15 is a diagram of a method for sensing bending angles through magnetic field coupling in accordance with an example. The method can include a calibration phase and an in use phase. In one aspect, an electromagnetic transmitting sensor can be disposed about a first body segment, and an electromagnetic receiving sensor can be disposed about a second body segment 1510. For example, the transmitting sensor can be disposed about a forearm of an individual, and the electromagnetic receiving sensor can be disposed about the corresponding arm of the individual. In another example, the transmitting sensor can be disposed about a thigh, and the electromagnetic receiving sensor can be disposed about the calf or ankle of the individual.

In one aspect, configuration data related to a magnetic field coupling between the transmitting sensor and the receiving sensor can be captured at a plurality of combinations of predetermined distances and orientations 1520. For example, a constant current can be driven in one or more coils of the transmitting sensor. With the constant current flowing through the one or more coils of the transmitting sensor, the electromagnetic transmitting and receiving sensors can be positioned at different distance and bending angles relative to each other. The receiving sensor can determine the signal strength of the open circuit voltage or the current induced in the one or more coils of the receiving sensor for each combination of distance and bending angles.

In one aspect, the configuration data can be stored in a data structure mapping magnetic field coupling between the transmitting sensor and the receiving sensor at the combinations of predetermined distances and orientations to reference angular displacements 1530. For example, the signal strength of the open circuit voltage or the current induced in the one or more coils of the receiving sensor can be recorded in a data storage device. For instance, the signal strength for each combination of distance and bending angle can be stored in a data structure mapping the signal strength to the corresponding of distance and bending angle. A calibration table data structure may not take much memory storage space. For example, if the bending angle detection range is from $0° \leq \theta_b \leq 130°$, with a resolution of $\Delta\theta_b = 1°$, and a distance range between the transmitting and receiving coils from d=20 cm to d=70 cm, with a resolution of $\Delta = 1$ cm, data stored as floating-point decimal values takes about 4 bytes for each value, and in such case the total storage consumed by such a calibration table would be approximately 26 KB.

In one aspect, use data related to the magnetic field coupling between the transmitting sensor and the receiving sensor can be captured 1540. For example, the transmitting sensor can drive a stable current in one or more coils of the transmitting sensor, and the receiving sensor can determine in real time the signal strength of the induced open circuit voltage or the induced current in the receiving sensor.

In one aspect, an angular displacement between the first body segment and the second body segment can be determined from the data structure mapping magnetic field coupling at the combinations of predetermined distances and orientations to reference angular displacements using the captured use data 1550. For example, the angular displacement can be determined by looking up the determined signal strength of the induced open circuit voltage or the induced current in the receiving sensor in the configuration data structure to determine the closest bending angle, or interpolating the bending angle from two or more of the configuration signal strength values in the configuration data structure.

In one aspect, the bending angle information can be output to a user visually on a display, audibly on a speaker, and/or stored in a computer storage device. The bending angle information can also be combined with other Human Activity Recognition (HAR) information from one or more other sensors. The bending angle information can be output and/or shared as Human Body Communication (HBC) and/or on a Body Area Network (BAN).

The system for sensing bending angles through magnetic field coupling can advantageously achieve a high resolution and wide range of bending angle measurements at low cost and low power consumption. The high-resolution sensing of bending angles between segments of the human body can be used in a variety of applications, including sports biomechanics, sports umpiring, office ergonomics for repetitive stress injuries (RSI), physical therapy, accident prevention and mitigation, and design and fitting of prosthetics.

EXAMPLES

The following examples pertain to specific technology embodiments and point out specific features, elements, or steps that may be used or otherwise combined in achieving such embodiments.

In one example, there is provided a system for sensing bending angles between body segments comprising: an electromagnetic transmitting sensor configured to be disposed about a first body segment; an electromagnetic receiving sensor configured to be disposed about a second body segment; and a first processing unit configured to capture data related to a magnetic field coupling between the electromagnetic transmitting sensor and the electromagnetic receiving sensor.

In one example of a system for sensing bending angles between body segments, the first processing unit is further configured to determine an angular displacement as a function of the captured data.

In one example of a system for sensing bending angles between body segments, the first processing unit is further configured to capture configuration data related to a magnetic field coupling between the electromagnetic transmitting sensor and the electromagnetic receiving sensor when the electromagnetic transmitting sensor and the electromagnetic receiving sensor are a predetermined distance and orientation with respect to each other, to capture use data related to a magnetic field coupling between the electromagnetic transmitting sensor and the electromagnetic receiving sensor, and to determine an angular displacement as a function of the captured use data and configuration data.

In one example of a system for sensing bending angles between body segments a first form factor includes the electromagnetic transmitting sensor; and a second form factor includes the electromagnetic receiving sensor.

In one example of a system for sensing bending angles between body segments, the second form factor further includes the first processing unit.

In one example of a system for sensing bending angles between body segments, the first form factor further includes the first processing unit.

In one example of a system for sensing bending angles between body segments, the first form factor and second form factor are selected from a group consisting of a wrist band, a watch, a bracelet, a ring, an arm band, a leg band, an anklet, a belt, a necklace, a choker, an earring, and a headband.

In one example of a system for sensing bending angles between body segments further comprises: a first communication interface to transfer the captured data from the first procession unit to a second processing unit.

In one example of a system for sensing bending angles between body segments further comprises: a second communication interface to receive the captured data from the first communication interface; and the second processing unit to determine an angular displacement as a function of the captured data.

In one example of a system for sensing bending angles between body segments further comprises: the first processing unit to capture configuration data related to a magnetic field coupling between the electromagnetic transmitting sensor and the electromagnetic receiving sensor when the electromagnetic transmitting sensor and the electromagnetic receiving sensor are a predetermined distance and orientation with respect to each other, and to capture use data related to a magnetic field coupling between the electromagnetic transmitting sensor and the electromagnetic receiving sensor; the first communication interface to transfer the captured configuration data and captured use data to a second communication interface; and a second processing unit to further determine an angular displacement as a function of the captured use data and configuration data.

In one example of a system for sensing bending angles between body segments further comprises: a first form factor including the electromagnetic transmitting sensor; a second form factor including the electromagnetic receiving sensor; and a third form factor including the second processing unit.

In one example of a system for sensing bending angles between body segments, the first form factor and second form factor are selected from a group consisting of a wrist band, a watch, a bracelet, a ring, an arm band, a leg band, an anklet, a belt, a necklace, a choker, an earring, and a headband; and the third form factor is selected from a group consisting of a smart phone, a smart watch, a tablet computing device, a laptop computing device, a desktop personal computer (PC), a portable music player, and a personal gaming device.

In one example of a system for sensing bending angles between body segments, the second processing unit is selected from a group consisting of a combinational logic circuit, a field programmable gate array (FPGA), an application specific integrated circuit (ASIC), a microcontroller, a mobile processor, a digital signal processor (DSP), and a central processing unit (CPU).

In one example of a system for sensing bending angles between body segments, a constant amplitude alternating current is driven through the first set of one or more coils.

In one example of a system for sensing bending angles between body segments, a constant amplitude alternating current is periodically driven through the first set of one or more coils.

In one example, there is provided a method for sensing bending angles between body segments comprising: disposing an electromagnetic transmitting sensor about a first body segment; disposing an electromagnetic receiving sensor about a second body segment; and capturing data related to a magnetic field coupling between the electromagnetic transmitting sensor and the electromagnetic receiving sensor.

In one example of a method for sensing bending angles between body segments further comprises: determining an angular displacement between the first body segment and the second body segment as a function of the captured data.

In one example of a method for sensing bending angles between body segments further comprises: capturing configuration data related to a magnetic field coupling between the electromagnetic transmitting sensor and the electromagnetic receiving sensor at combinations of predetermined distances and orientations; capturing use data related to a magnetic field coupling between the electromagnetic transmitting sensor and the electromagnetic receiving sensor; and determining an angular displacement between the first body segment and the second body segment as a function of the captured use data and the captured configuration data.

In one example of a method for sensing bending angles between body segments further comprises: storing the captured configuration data in a data structure mapping magnetic field coupling between the electromagnetic transmitting sensor and the electromagnetic receiving sensor at the combinations of predetermined distances and orientations to reference angular displacements; and determining the angular displacement between the first body segment and the second body segment from the data structure mapping magnetic field coupling between the electromagnetic transmitting sensor and the electromagnetic receiving sensor at the combinations of predetermined distances and orientations to reference angular displacements using the captured use data.

In one example of a method for sensing bending angles between body segments further comprises: driving a current with a constant peak-to-peak amplitude through the electromagnetic transmitting sensor.

In one example, there is provided a real-time system for sensing bending angles between body segments comprising: a transmitting sensor including, a first set of one or more coils disposed about a first body segment; and a current source to drive a current having a predetermined frequency and predetermined peak-to-peak amplitude through the first set of one or more coils to radiate an electromagnetic field; and a receiving sensor including, a second set of one or more coils disposed about a second body segment; and a voltage detector to determine an open circuit voltage induced in the second set of one or more coils by the electromagnetic field radiated from the first set of one or more coils.

In one example a real-time system for sensing bending angles between body segments further comprises: the receiving sensor further including, a processing unit to measure an angular displacement between the first body segment and the second body segment as a function of the open circuit voltage induced in the second set of one or more coils.

In one example a real-time system for sensing bending angles between body segments further comprises: the receiving sensor further including, a first communication interface for transmitting the determined open circuit voltage induced in the second set of one or more coils to a processing unit; and the processing unit to measure an angular displacement between the first body segment and the second body segment as a function of the open circuit voltage induced in the second set of one or more coils.

In one example a real-time system for sensing bending angles between body segments further comprises: the transmitting sensor further including, the current source to drive the current having a predetermined duty cycle.

In one example, there is provided a real-time system for sensing bending angles between body segments comprising: a transmitting sensor including, a first set of one or more coils disposed about a first body segment; and a current source to drive a current having a predetermined frequency and predetermined peak-to-peak amplitude through the first set of one or more coils to radiate an electromagnetic field; and a receiving sensor including, a second set of one or more coils disposed about a second body segment; and a current detector to determine a current induced in the second set of one or more coils by the electromagnetic field radiated from the first set of one or more coils.

In one example a real-time system for sensing bending angles between body segments further comprises: the receiving sensor further including, a processing unit to measure an angular displacement between the first body segment and the second body segment as a function of the current induced in the second set of one or more coils.

In one example a real-time system for sensing bending angles between body segments further comprises: the receiving sensor further including, a first communication interface for transmitting the determined current induced in the second set of one or more coils to a processing unit; and the processing unit to measure an angular displacement between the first body segment and the second body segment as a function of the current induced in the second set of one or more coils.

In one example a real-time system for sensing bending angles between body segments further comprises: the transmitting sensor further including, the current source to drive the current having a predetermined duty cycle.

While the forgoing examples are illustrative of the principles of the present technology in one or more particular applications, it will be apparent to those of ordinary skill in the art that numerous modifications in form, usage and details of implementation can be made without the exercise of inventive faculty, and without departing from the principles and concepts of the technology.

What is claimed is:

1. A system for sensing bending angles between body segments comprising:
   an electromagnetic transmitting sensor configured to be disposed about a first body segment;
   an electromagnetic receiving sensor configured to be disposed about a second body segment; and
   a first processing unit configured to capture data related to a magnetic field coupling between the electromagnetic transmitting sensor and the electromagnetic receiving sensor when the electromagnetic transmitting sensor and the electromagnetic receiving sensor are a predetermined distance and orientation with respect to each other, to capture use data related to a magnetic field coupling between the electromagnetic transmitting sensor and the electromagnetic receiving sensor, and to determine an angular displacement as a function of the captured use data and configuration data.

2. The system according to claim 1, further comprising: the first processing unit to determine an angular displacement as a function of the captured data.

3. The system of claim 1, further comprising:
   a first form factor including the electromagnetic transmitting sensor; and
   a second form factor including the electromagnetic receiving sensor.

4. The system of claim 3, wherein the second form factor further includes the first processing unit.

5. The system of claim 3, wherein the first form factor further includes the first processing unit.

6. The system of claim 3, wherein the first form factor and second form factor are selected from a group consisting of a wrist band, a watch, a bracelet, a ring, an arm band, a leg band, an anklet, a belt, a necklace, a choker, an earing, and a headband.

7. The system according to claim 1, further comprising:
   a first communication interface to transfer the captured data from the first procession unit to a second processing unit.

8. The system according to claim 7, further comprising
   a second communication interface to receive the captured data from the first communication interface; and
   the second processing unit to determine an angular displacement as a function of the captured data.

9. The system according to claim 7, further comprising:
   the first processing unit to capture configuration data related to a magnetic field coupling between the electromagnetic transmitting sensor and the electromagnetic receiving sensor when the electromagnetic transmitting sensor and the electromagnetic receiving sensor are a predetermined distance and orientation with respect to each other, and to capture use data related to a magnetic field coupling between the electromagnetic transmitting sensor and the electromagnetic receiving sensor;
the first communication interface to transfer the captured configuration data and captured use data to a second communication interface; and
a second processing unit to further determine an angular displacement as a function of the captured use data and configuration data.

10. The system of claim 8, further comprising:
a first form factor including the electromagnetic transmitting sensor;
a second form factor including the electromagnetic receiving sensor; and
a third form factor including the second processing unit.

11. The system of claim 10, wherein,
the first form factor and second form factor are selected from a group consisting of a wrist band, a watch, a bracelet, a ring, an arm band, a leg band, an anklet, a belt, a necklace, a choker, an earing, and a headband; and
the third form factor is selected from a group consisting of a smart phone, a smart watch, a tablet computing device, a laptop computing device, a desktop personal computer (PC), a portable music player, and a personal gaming device.

12. The system of claim 8, wherein the second processing unit is selected from a group consisting of a combinational logic circuit, a field programmable gate array (FPGA), an application specific integrated circuit (ASIC), a microcontroller, a mobile processor, a digital signal processor (DSP), and a central processing unit (CPU).

13. The system of claim 1, wherein a constant amplitude alternating current is driven through a first set of one or more coils.

14. The system of claim 1, wherein a constant amplitude alternating current is periodically driven through a first set of one or more coils.

15. A method for sensing bending angles between body segments comprising:
disposing an electromagnetic transmitting sensor about a first body segment;
disposing an electromagnetic receiving sensor about a second body segment;
capturing data related to a magnetic field coupling between the electromagnetic transmitting sensor and the electromagnetic receiving sensor;
capturing configuration data related to a magnetic field coupling between the electromagnetic transmitting sensor and the electromagnetic receiving sensor at combinations of predetermined distances and orientations;
capturing use data related to a magnetic field coupling between the electromagnetic transmitting sensor and the electromagnetic receiving sensor; and
determining an angular displacement between the first body segment and the second body segment as a function of the captured use data and the captured configuration data.

16. The method of claim 15, further comprising:
determining an angular displacement between the first body segment and the second body segment as a function of the captured data.

17. The method of claim 15, further comprising:
storing the captured configuration data in a data structure mapping magnetic field coupling between the electromagnetic transmitting sensor and the electromagnetic receiving sensor at the combinations of predetermined distances and orientations to reference angular displacements; and
determining the angular displacement between the first body segment and the second body segment from the data structure mapping magnetic field coupling between the electromagnetic transmitting sensor and the electromagnetic receiving sensor at the combinations of predetermined distances and orientations to reference angular displacements using the captured use data.

18. The method of claim 15, further comprising:
driving a current with a constant peak-to-peak amplitude through the electromagnetic transmitting sensor.

19. A real-time system for sensing bending angles between body segments comprising:
a transmitting sensor including,
a first set of one or more coils disposed about a first body segment; and
a current source to drive a current having a predetermined frequency and predetermined peak-to-peak amplitude through the first set of one or more coils to radiate an electromagnetic field; and
a receiving sensor including,
a second set of one or more coils disposed about a second body segment; and
a voltage detector to determine an open circuit voltage induced in the second set of one or more coils by the electromagnetic field radiated from the first set of one or more coils.

20. The system according to claim 19, further comprising:
the receiving sensor further including,
a processing unit to measure an angular displacement between the first body segment and the second body segment as a function of the open circuit voltage induced in the second set of one or more coils.

21. The system according to claim 19, further comprising:
the receiving sensor further including,
a first communication interface for transmitting the determined open circuit voltage induced in the second set of one or more coils to a processing unit; and
the processing unit to measure an angular displacement between the first body segment and the second body segment as a function of the open circuit voltage induced in the second set of one or more coils.

22. The system according to claim 19, further comprising:
the transmitting sensor further including, the current source to drive the current having a predetermined duty cycle.

23. A real-time system for sensing bending angles between body segments comprising:
a transmitting sensor including,
a first set of one or more coils disposed about a first body segment; and
a current source to drive a current having a predetermined frequency and predetermined peak-to-peak amplitude through the first set of one or more coils to radiate an electromagnetic field; and
a receiving sensor including,
a second set of one or more coils disposed about a second body segment; and
a current detector to determine a current induced in the second set of one or more coils by the electromagnetic field radiated from the first set of one or more coils.

24. The system according to claim 23, further comprising:
the receiving sensor further including, a processing unit to measure an angular displacement between the first body segment and the second body segment as a function of the current induced in the second set of one or more coils.

25. The system according to claim 23, further comprising:
the receiving sensor further including,
a first communication interface for transmitting the determined current induced in the second set of one or more coils to a processing unit; and
the processing unit to measure an angular displacement between the first body segment and the second body segment as a function of the current induced in the second set of one or more coils.

26. The system according to claim 23, further comprising:
the transmitting sensor further including,
the current source to drive the current having a predetermined duty cycle.

* * * * *